United States Patent
González Serrano et al.

(10) Patent No.: US 9,905,002 B2
(45) Date of Patent: Feb. 27, 2018

(54) METHOD AND SYSTEM FOR DETERMINING THE PROGNOSIS OF A PATIENT SUFFERING FROM PULMONARY EMBOLISM

(71) Applicants: UNIVERSIDAD POLITÉCNICA DE MADRID, Madrid (ES); MASSACHUSETTS INSTITUTE OF TECHNOLOGY, Cambridge, MA (US); BRIGHAM AND WOMEN'S HOSPITAL, Boston, MA (US)

(72) Inventors: Germán González Serrano, Cambridge, MA (US); Daniel Jiménez Carretero, Madrid (ES); Frank John Rybicki, Boston, MA (US); María J. Ledesma Carbayo, Madrid (ES); Sara Rodríguez López, Madrid (ES); Raúl San José Estépar, Boston, MA (US)

(73) Assignees: UNIVERSIDAD POLITÉCNICA DE MADRID, Madrid (ES); MASSACHUSETTS INSTITUTE OF TECHNOLOGY, Cambridge, MA (US); BRIGHAM AND WOMEN'S HOSPITAL, Boston, MA (US)

( * ) Notice: Subject to any disclaimer, the term of this patent is extended or adjusted under 35 U.S.C. 154(b) by 0 days.

(21) Appl. No.: 15/026,401

(22) PCT Filed: Nov. 27, 2014

(86) PCT No.: PCT/EP2014/075840
§ 371 (c)(1),
(2) Date: Mar. 31, 2016

(87) PCT Pub. No.: WO2015/078980
PCT Pub. Date: Jun. 4, 2015

(65) Prior Publication Data
US 2016/0260210 A1  Sep. 8, 2016

Related U.S. Application Data

(60) Provisional application No. 61/909,574, filed on Nov. 27, 2013.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/7271* (2013.01); *G06K 9/4604* (2013.01);
(Continued)

(58) Field of Classification Search
CPC . A61B 5/7271; G06F 19/3437; G06F 19/345; G06K 2209/051; G06K 9/4604;
(Continued)

(56) References Cited

U.S. PATENT DOCUMENTS

2006/0239554 A1\* 10/2006 Sun ..................... G06T 19/00
                                                        382/173
2008/0205724 A1\*  8/2008 Cocosco ............... G06K 9/342
                                                        382/130

(Continued)

OTHER PUBLICATIONS

Apfaltrer, Paul, et al. "Prognostic value of perfusion defect volume at dual energy CTA in patients with pulmonary embolism: correlation with CTA obstruction scores, CT parameters of right ventricular dysfunction and adverse clinical outcome." European journal of radiology 81.11 (2012): 3592-3597.\*

(Continued)

*Primary Examiner* — Li Liu
(74) *Attorney, Agent, or Firm* — Reising Ethington P.C.

(57) ABSTRACT

A system for determining the prognosis of a patient suffering from pulmonary embolism is provided. The system may include at least one computer system configure to receive patient specific data regarding his pulmonary embolism status. The at least one computer system may be further configured to create a model of the patient's heart, with at least information of the two ventricles, and to determine the ratio of sizes of the ventricles. The system will then report such ratio to the clinician or report a risk index of clinical outcome for such patient.

16 Claims, 12 Drawing Sheets

(51) Int. Cl.
| | | |
|---|---|---|
| G06K 9/62 | (2006.01) | |
| A61B 5/00 | (2006.01) | |
| G06K 9/46 | (2006.01) | |
| G06K 9/52 | (2006.01) | |
| G06K 9/66 | (2006.01) | |
| G06T 7/60 | (2017.01) | |
| G06T 15/08 | (2011.01) | |
| G06T 17/00 | (2006.01) | |
| G06T 7/70 | (2017.01) | |
| G06T 7/73 | (2017.01) | |
| G06T 7/13 | (2017.01) | |
| G06T 7/62 | (2017.01) | |
| G06F 19/00 | (2018.01) | |

(52) U.S. Cl.
CPC ............ *G06K 9/4661* (2013.01); *G06K 9/52* (2013.01); *G06K 9/6215* (2013.01); *G06K 9/6218* (2013.01); *G06K 9/6262* (2013.01); *G06K 9/6277* (2013.01); *G06K 9/66* (2013.01); *G06T 7/13* (2017.01); *G06T 7/60* (2013.01); *G06T 7/62* (2017.01); *G06T 7/70* (2017.01); *G06T 7/75* (2017.01); *G06T 15/08* (2013.01); *G06T 17/00* (2013.01); *G06F 19/345* (2013.01); *G06F 19/3437* (2013.01); *G06K 2209/051* (2013.01); *G06T 2200/04* (2013.01); *G06T 2207/10081* (2013.01); *G06T 2207/20081* (2013.01); *G06T 2207/20161* (2013.01); *G06T 2207/30048* (2013.01)

(58) Field of Classification Search
CPC ...... G06K 9/4661; G06K 9/52; G06K 9/6215; G06K 9/6218; G06K 9/6262; G06K 9/6277; G06K 9/66; G06T 15/08; G06T 17/00; G06T 2200/04; G06T 2207/10081
See application file for complete search history.

(56) References Cited

U.S. PATENT DOCUMENTS

| | | | |
|---|---|---|---|
| 2008/0292169 A1* | 11/2008 | Wang | G06T 7/0012 382/131 |
| 2012/0281895 A1* | 11/2012 | Chono | A61B 8/461 382/128 |
| 2013/0266197 A1* | 10/2013 | Nagenthiraja | G06T 7/0012 382/128 |

OTHER PUBLICATIONS

Lu, Michael T., et al. "Axial and reformatted four-chamber right ventricle-to-left ventricle diameter ratios on pulmonary ct angiography as predictors of death after acute pulmonary embolism." American Journal of Roentgenology198.6 (2012): 1353-1360.*
Masutani, Yoshitaka, Heber MacMahon, and Kunio Doi. "Computerized detection of pulmonary embolism in spiral CT angiography based on volumetric image analysis." IEEE Transactions on Medical Imaging 21.12 (2002): 1517-1523.*
"Automated volumetric analysis of four cardiac chambers in pulmonary embolism", New Technologies, Diagnostic Tools and Drugs, Thromb Haemost 2012; 108: 384-393, Jun. 28, 2012.
"Describing complicated objects by implicit polynomials", IEEE Transactions on Pattern Analysis and Machine Intelligence, vol. 16, No. 1, Jan. 1, 1994.
"Estimation of planar curves, surfaces, and nonplanar space curves defined by implicit equations with applications to edge and range image segmentation", IEEE Transactions on Pattern Analysis and Machine Intelligence, vol. 13, No. 11, Nov. 1, 1991.
"Using hyperquadrics for shape recovery from range data", Proceedings of the International Conference on Computer Vision. Berlin, Conf. 4, May 11, 1993.
"Four-Chamber Heart Modeling and Automatic Segmentation for 3-D Cardiac CT Volumes Using Marginal Space Learning and Steerable Features", IEEE Transactions on Medical Imaging, vol. 27, No. 11, Nov. 1, 2008.
"Multi-scale line segmentation with automatic estimation of width, contrast and tangential direction in 2d and 3d medical images", Joint Conference. Computer Vision, Virtual Reality and Roboticsin Medicine and Medical Robotics and Computer-Assisted Surgery Proceedings, Jan. 1.
"The OpenCV Reference Manual", Jul. 1, 2013.
"Automatic Delineation of the Myocardial Wall From CT Images Via Shape Segmentation and Variational Region Growing", IEEE Transactions on Biomedical Engineering, vol. 60, No. 10, Oct. 1, 2013.
"Marginal Space Learning for Efficient Detection of 2D/3D Anatomical Structures in Medical Images", Jul. 5, 2009, Information Processing in Medical Imaging, Springer Berlin Heidelberg.
"Comparison of EGG-gated versus non-gated CT ventricular measurements in thirty patients with acute pulmonary embolism", The International Journal of Cardiac Imaging, Kluwer Academic Publishers, vol. 25, No. 1, Jul. 15, 2008.
International Search Report and Written Opinion dated May 20, 2015 for application No. PCT/EP2014/075840; 7 pages.

* cited by examiner

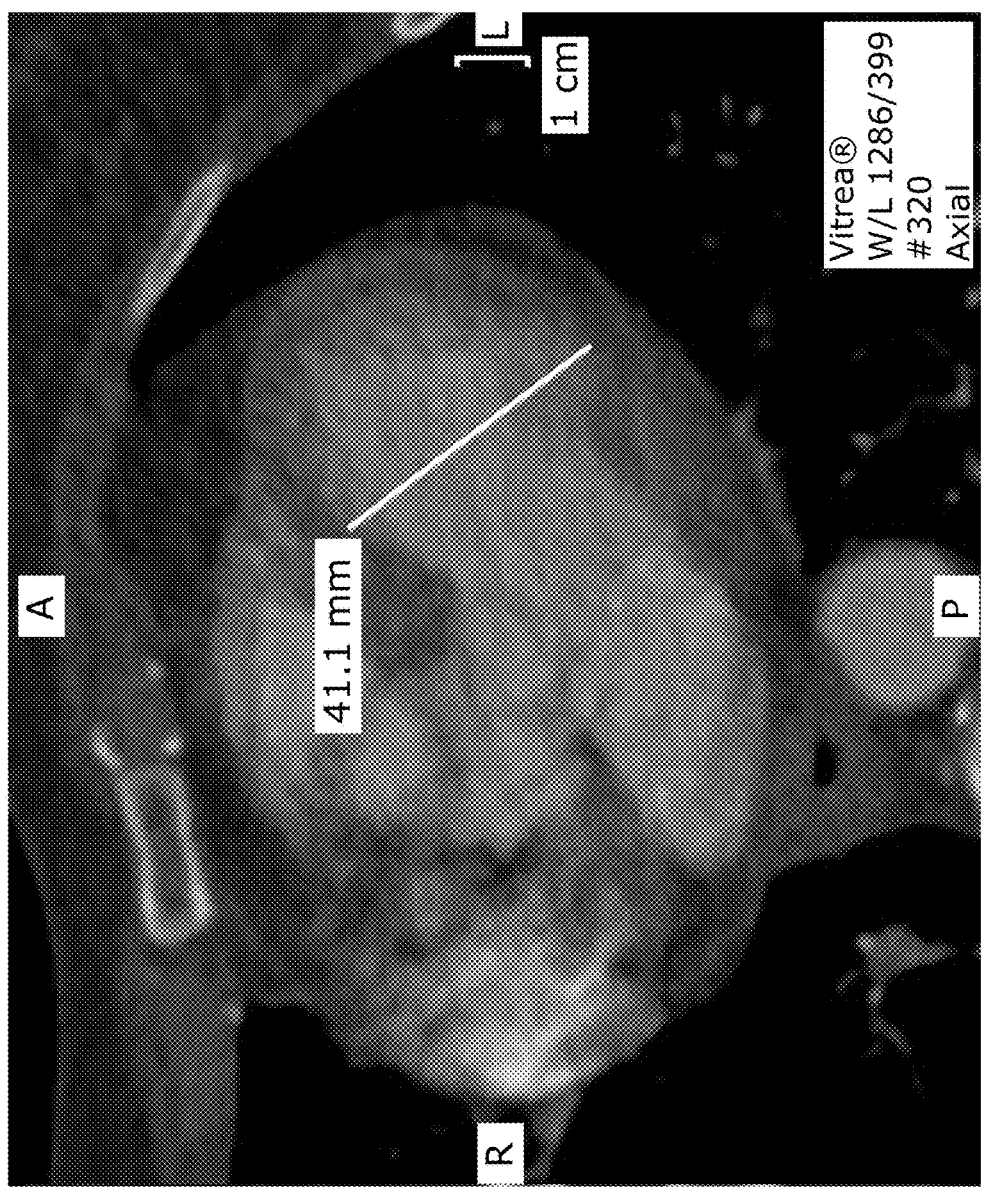
Figure 2. Continuation

Figure 2. Continuation

Figure 2. Continuation

METHOD AND SYSTEM FOR DETERMINING THE PROGNOSIS OF A PATIENT SUFFERING FROM PULMONARY EMBOLISM

TECHNICAL FIELD

This application pertains generally to predicting patient outcomes, and more specifically, to a method and system for determining the prognosis of a patient suffering from a pulmonary embolism.

BACKGROUND

Pulmonary embolism (PE) is a common disease with an incidence greater than 1 per 1000 and a three month mortality rate of 15%. Several treatments are available for PE, ranging from prophylactic anticoagulants to surgical embolectomy. Accurate patient treatment relies on proper risk stratification, which is done based on (i) clinical evaluation, (ii) determination of cardiac biomarkers levels such as troponin, and (iii) estimation of right ventricular size and/or function. PE increases the resistance of the pulmonary arteries. Depending on the extent of the disease and the general health of the patient, the right ventricle can compensate for such extra strain. Uncompensated pressure can result in right ventricular hypokinesis, which can lead to right ventricular enlargement among other issues.

Diagnosis of PE may be done with Computed Tomography Pulmonary Angiography (CTPA). Generally, the patient is injected with iodine contrast and imaged in a CT scan to evaluate opacifications in the pulmonary arteries. The cardiac chambers are included in standard CTPAs, therefore information on the state of the heart can be obtained without altering the current diagnostic protocol. The right ventricular to left ventricular diameter ratio (RV/LV), introduced more than 15 years ago, has been proven as a predictor of mortality in patients with severe PE.

Quantification of the RV/LV ratio can be done via several methods, such as volumetric measurements, diameter measurements in four chambers reformatting or in axial slices. Measuring on axial slices has been shown to be equivalent to measurements in 4 chamber views. Such measurements are often time consuming. To prevent increasing radiologist time, recent research has focused on qualitative evaluation of right ventricular enlargement as a biomarker for prognosis. However, such measurement is based on the experience of the reading radiologists.

In addition, other objects, desirable features and characteristics will become apparent from the subsequent summary and detailed description, and the appended claims, taken in conjunction with the accompanying drawings and this background.

SUMMARY

According to various embodiments, provided is an objective RV/LV metric that does not incur in an extra radiologist burden and is able to predict patient outcome. The RV/LV diameter ratio is a proven metric of prognosis in patients with CT pulmonary angiography (CTPA) findings of acute pulmonary embolism (PE). The various teachings of the present disclosure provide a completely automated algorithm to output the axial right ventricular to left ventricular (RV/LV) diameter ratio from CTPA images.

According to various embodiments, a completely automated algorithm with the following method was designed to compute the RV/LV diameter ratio. In various embodiments, the method includes: image pre-processing, right and left heart detection based on machine-learning techniques, detection on clustering and seed positioning, septum detection, right and left heart segmentation based on level-sets with curvature constraints and edge priors, and caliper positioning and ratio computation. This exemplary algorithm was tested in 198 consecutive patients with acute PE diagnosed with CTPA using (a) reference standard RV/LV radiologist measurements and (b) 30-day PE-specific mortality (c) 30-day PE-specific mortality plus the need for intensive therapies.

The algorithm of the present disclosure correctly placed the RV and LV diameters in the ventricles in 92.4% (183/198) of CTPA studies. Using radiologist reference standard, the correlation between the RV/LV diameter ratio obtained by the algorithm and that obtained by the radiologist was high (r=0.81). Compared to the radiologist, the algorithm equally achieved high accuracy in predicting 30-day PE-specific mortality plus the need for intensive therapies, with area under the curve of 0.75 for the automated method and 0.78 for the radiologist measurements. Similar results were found for 30-days PE-specific mortality, with areas under the curve of 0.72 for the automated method and 0.75 for the manual one.

Thus, an automated algorithm for determining the CT derived RV/LV diameter ratio in patients with acute PE according to the various embodiments of the present disclosure has high accuracy when compared to measurements made by a radiologist and prognostic significance when tested against reference standard outcomes.

A person skilled in the art can gather other characteristics and advantages of the disclosure from the following description of exemplary embodiments that refers to the attached drawings, wherein the described exemplary embodiments should not be interpreted in a restrictive sense.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the present disclosure or the application and uses of the present disclosure. Furthermore, there is no intention to be bound by any theory presented in the preceding background or the following detailed description.

CAD Method

Figure 1:
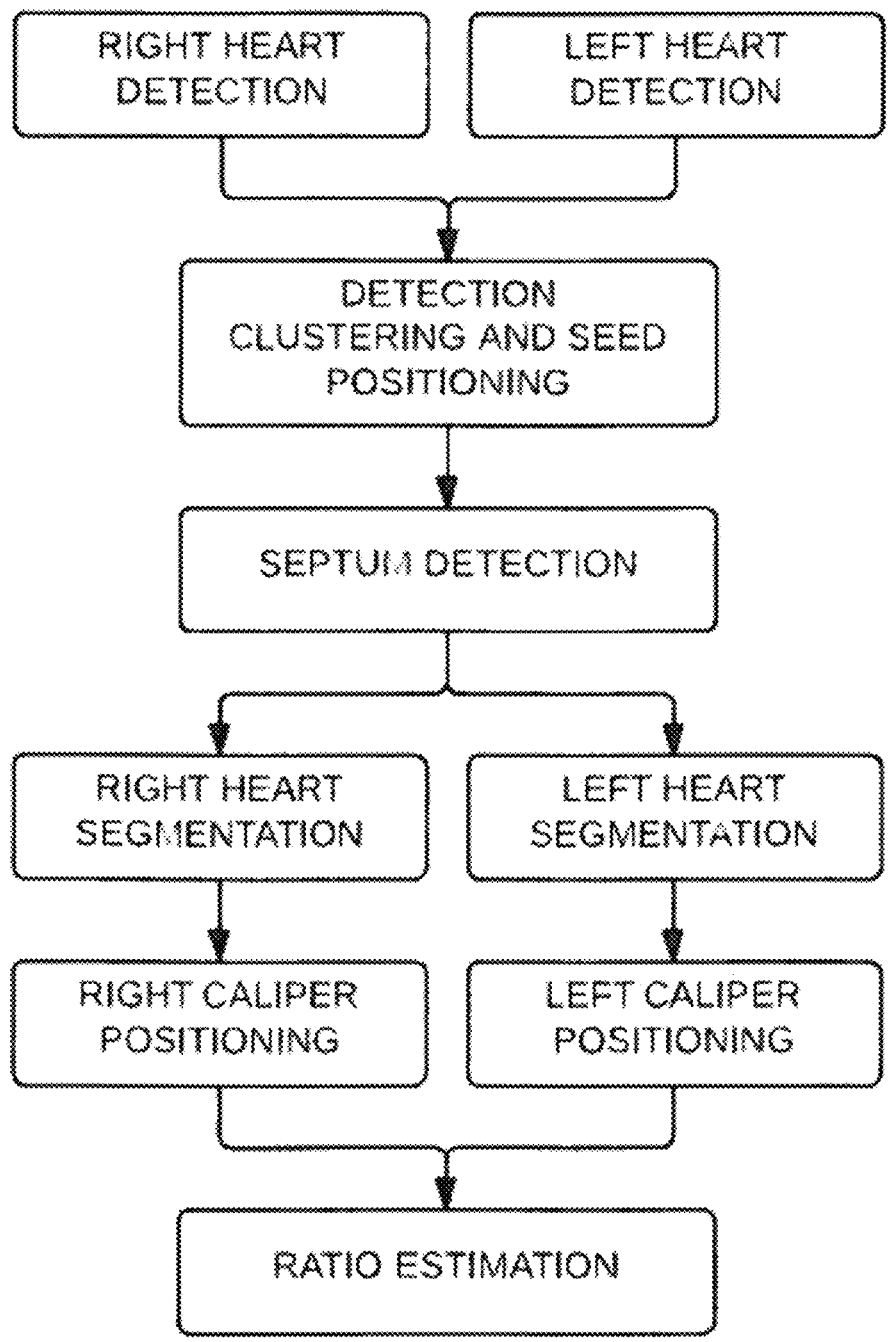
FIG. 1 is an exemplary block diagram of the algorithm of the present disclosure according to various embodiments.

A completely automated algorithm, sketched on FIG. 1, is designed to compute the RV/LV axial diameter ratio. The algorithm may be implemented by a computer system that includes a non-transitory, tangible storage medium readable by a processing circuit and storing instructions for execution by the processing circuit for performing the algorithm. In the algorithm, the right and left heart ventricles detection is performed based on machine-learning techniques. The detections are clustered to place points (seeds) in the ventricles. The septum is then estimated using the location of the seeds and image properties. The right and left ventricles are then segmented using a level-sets technique with curvature constraints. Finally, the diameters of the ventricles are measured and the ratio of the calipers computed.

Ventricle Detection

This step automatically locates the area where heart ventricles are visible in each axial slice of the CTPA image using a general machine learning based system for detecting objects in 2D images. The algorithm is trained to detect two different shapes, corresponding to the right and left ventricles. The training set comprised 40 CTPAs from another institution: UCR (Unidad Central de Radiodiagnostico, Madrid, Spain) that are available for research in the scope of the ISBI 2013 CAD-PE Challenge. The training set is formed by axial images labeled with bounding boxes around the ventricles (positive training samples) and images where the heart is not visible (negatives training images). The output of the detection algorithm is a set of 2-dimensional bounding boxes per axial slice, containing structures similar to the models of the ventricles that the algorithm learned. A score per detection representing the fitness of the detection to the model is kept for further processing.

Detection Clustering

Only a subset of the detections truly represents the ventricles. To find such subset, we first eliminate detections that are not coherent with statistics on the location and size of the heart inferred from the training dataset. Remaining detections across axial slices are linked using an unsupervised clustering algorithm based on the MeanShift technique. The features used to compute similarities between detections and to cluster them are the position of the detections, their size and their aspect ratio. Different clusters are then ranked according to a function based on the fitness scores of the detections and the density of detections in each cluster. Only the highest-ranking cluster is kept for each ventricle. Each detection in the surviving cluster is used to establish a seed point, which is assumed to lie in the ventricle. Such seed points will be used to detect the septum and to initiate the segmentation algorithm.

Septum Detection

Accurate detection of the interventricular septum is key for the proper functioning of the algorithm, since it avoids leakages in the segmentation stage and allows measuring the ventricular diameters perpendicularly to the interventricular septum. According to various embodiments, the interventricular septum is modeled as a 3-dimensional plane, which may be a simplification. The plane is located by analyzing second-order image derivatives, combined to detect plane-like geometrical structures and the direction of such plane-like structure. According to various embodiments, the maximum score of such plane-like structure detection algorithm in image locations is searched for between the seeds placed for the right and for the left ventricles. The location and orientation of such maximum defines univocally a 3-dimensional plane, which represents our estimation of the interventricular septum.

Ventricle Segmentation

A 3D level-set algorithm initially developed for liver segmentation was successfully adapted to the automatic segmentation of heart ventricles. The underlying idea of active contour models is to detect objects by evolving a contour from a set of seed points subject to image constraints. Local curvature constraints applied at the estimated interventricular septum and edge priors were used to improve the segmentation results. The parameters of the level-set method were fixed using the first 10 cases of the evaluation dataset. The same level-set parameters were used to segment the ventricles in all CTPA images.

Caliper Positioning and Ratio Estimation

Once the 3D ventricular segmentations have been computed, the ventricular diameters are estimated as the largest magnitude of the intersection of perpendicular lines to the septum with the resulting segmentation in each 2D axial slice in the selected cluster. However, due to poor image contrast and especially in the right side of the heart, ventricle segmentations can include parts of the atriums. To prevent placing calipers in the atriums, the shape of the segmentation is analyzed to find the atrioventricular valves by fitting an n-th order polynomial to the contour of the segmentation and analyzing its roots and derivatives in each axial slice. Only calipers between the estimated atrioventricular valve and the apex are considered. Finally RV/LV diameter ratio is calculated as the division of the largest calipers for both right and left ventricles.

Risk Evaluation

A risk index of a clinical outcome for that patient is computed using both information inferred from images of the patient and clinical information. Examples of information extracted from patient's images may include, but is not limited to, RV/LV axial diameter ratio, lung size, aorta size, vasculature volume, bronqui size, etc. Examples of clinical information may include, but are not limited to, pulse, blood pressure, arterial pressure, oxygenation level, other conditions, malignancies, etc. Methods to combine imaging and clinical information may be, but is not limited to, support vector machines, neural networks, decision trees, boosting, etc.

Interface

Figure 7:
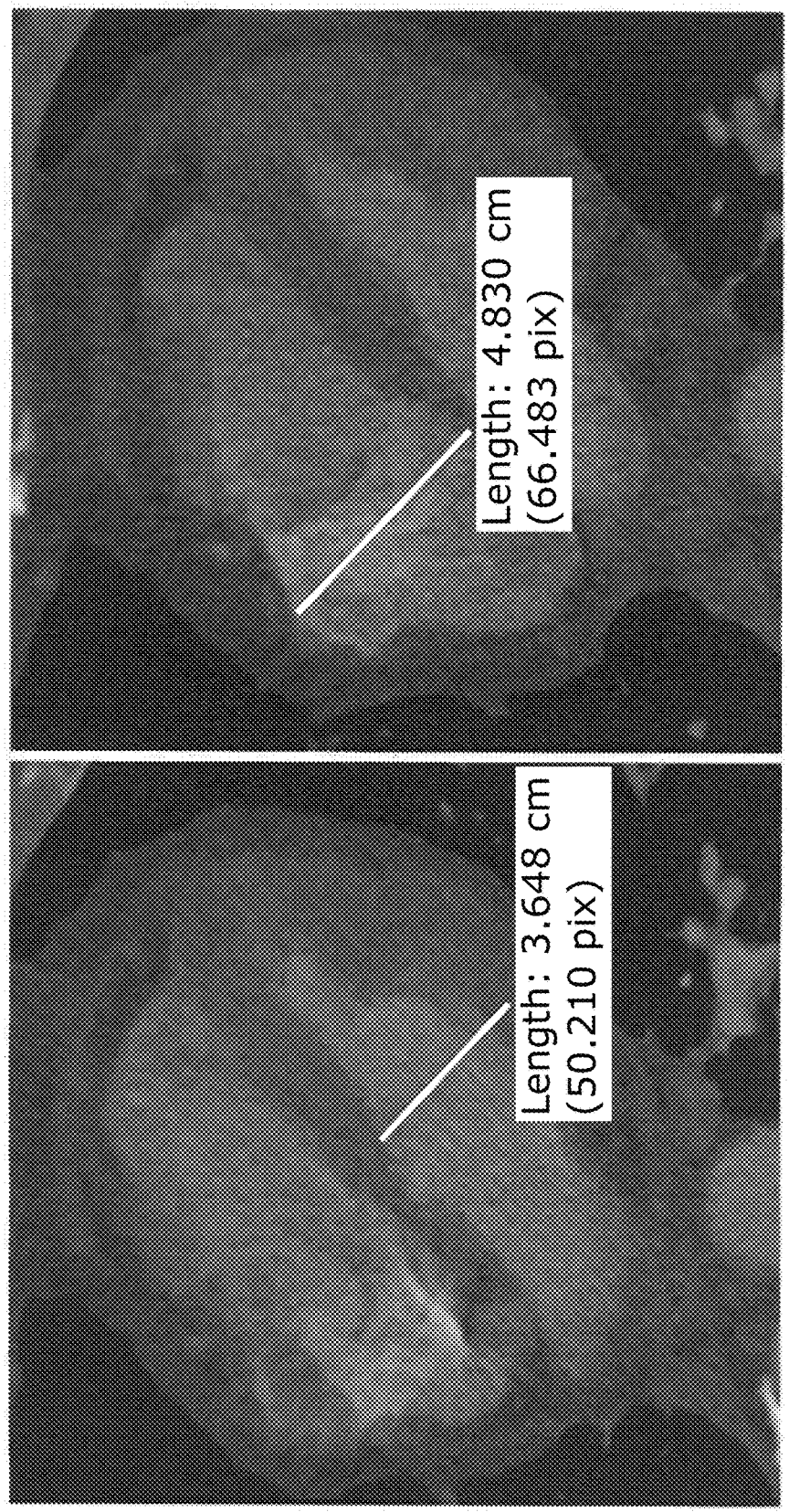
FIG. 7 is an exemplary interface used to display the axial RV/LV diameter ratio.

An interface to evaluate the information automatically extracted from the images is presented on FIG. 7. In various embodiments, the interface will show on the left the image of the right ventricle with the right ventricular diameter estimation overlaid, and on the right the image of the left ventricle with the left ventricle diameter estimation overlaid. In various embodiments, segmentations of the different organs will be shown in planar, axial and sagittal cuts of the images. The operator can or cannot modify and alter the automated markings on the images, with the subsequent actualization of the measured quantities.

Integration with the PACS System of the Hospital

The system can be integrated with the hospital picture archiving system in such a way that it will retrieve any image conforming to any given imaging protocol and analyze it without operator interaction. The results of the analysis can be stored in the electronic medical record for the patient.

Evaluation

Database

We evaluated 198 cases from a retrospective acute PE study. CTPA examinations were performed over a 10-month period beginning February 2009 at a single, urban, academic institution, under the approval of a HIPAA-compliant study by an Institutional Review Board. All study participants provided written informed consent before enrollment. The mean age was 60±16 years (range 22-89), 112 patients were female and 86 were male. Imaging data from two cases of the original study were not available at the time of the analysis.

For each patient, death was determined from the social security death index. 32 deaths within 30 days were reported and, of those, 22 were PE-related deaths. Additionally the delivery of intensive therapies during the initial hospitalization was obtained from hospital electronic medical records: 13 patients who did not die within 30 days received intensive therapies and 5 of them needed more than one. The therapeutic interventions were: thrombolysis (n=7), vasopressor therapy for systemic arterial hypotension (n=4), mechanical ventilation (n=3), catheter intervention or surgical embolectomy (n=4). Two outcomes are defined to test the predictive value of the automated axial RV/LV diameter ratio: PE-related death within 30 days (n=22) and a composite outcome consisting on the PE-related death within 30 days or the need for intensive therapies (n=35). No patient was lost to follow-up.

Image Acquisition

CTPA for every patient was acquired with 16-slice or 64-slice scanners (Siemens Healthcare, Erlangen, Germany) and the images were reconstructed at 1.0 mm slice thickness. Scanning parameters included 80-120 kVp and an effective mAs of approximately 200. All patients received 75 mL of iodinated contrast media (370 mg iodine/mL) by using a power injector at a rate of 3 mL/s. Moreover, the acquisition was triggered with bolus tracking on the main pulmonary artery with a threshold of 80 HU.

Manual Assessment of RV/LV Ratio

Images were reviewed by a radiologist with 10-years of experience in cardiovascular imaging. For each case, RV/LV diameter ratio was calculated on axial images using a Vitrea fX 3.1 workstation (Vital Images, Minnetonka, Minn.). RV and LV diameters were defined as the largest distance between the surface of the interventricular septum and the endocardium within all axial slices in the heart region. Those RV and LV maximum diameters may be found at different craniocaudal levels. Another radiologist with 5-years of experience repeated the same measurements independently in 30 randomly selected scans to assess inter-subject variability.

Statistical Analysis

The resulting RV and LV diameters are visualized to determine if they are placed in the ventricles. Aggregated statistics are computed for the correctly placed diameter ratios of the automated method and for all the diameter ratios manually defined by the radiologists. When the analysis required paired measurements, only the manually defined ratios corresponding to the correctly placed diameters obtained with the automated method are taken into account.

Aggregated statistics of radiologists' RV, LV and RV/LV diameter ratio and those of the automated method are computed for their comparison. Paired t-tests of their means are used to analyze statistically significant difference between the measurements. Bland-Altman plot, Pearson's and Spearman's correlation coefficients are calculated for the automated and manual RV/LV diameter ratios and to compute inter-radiologists variability. The distributions of RV/LV diameter ratios for the different measurement methods conditioned on different medical outcomes are summarized by their mean. Statistical significance among such distributions is evaluated using Wilcoxon ranks sum tests.

The predictive value of the manually and the automatically computed RV/LV diameter ratios is established using a logistic regression model adjusted for age and sex. Likelihood ratio tests are performed to establish the relevance of each variable in the prediction of medical outcome.

Receiver-operating characteristic (ROC) analysis compared the accuracy of such models for predicting (i) PE-related death in 30 days and (ii) a composite outcome of PE-related 30-day mortality or the need for 1 or more intensive therapies. The areas under the curves (AUC) are to measure accuracy of the models. Statistical significance for model comparison are established using Chi-Square goodness of fit tests.

Results

The algorithm correctly detected both ventricles in 96% (190/198) of the CTPA studies. RV and LV diameters were placed in the atriums in 3.7% of the correctly detected cases (4 times in the RA and 3 times in the LA). A total of 92.4% (183/198) studies obtained correctly automated calipers in the ventricles.

Comparison Against Manually Computed RV/LV Ratio

Table 1 compares aggregated statistics of the automated and manually estimated diameters and ratios.

TABLE 1

Mean value for the automated and manually ventricular diameter estimations and RV/LV diameter ratios.
P-values obtained with a paired t-test of the means.

| | RV (mm) | p-value | LV (mm) | p-value | RV/LV | p-value |
|---|---|---|---|---|---|---|
| Manual | 47.9 | <0.001 | 44.6 | <0.001 | 1.10 | 0.08 |
| Automated | 43.2 | | 42.3 | | 1.08 | |

Figure 2:
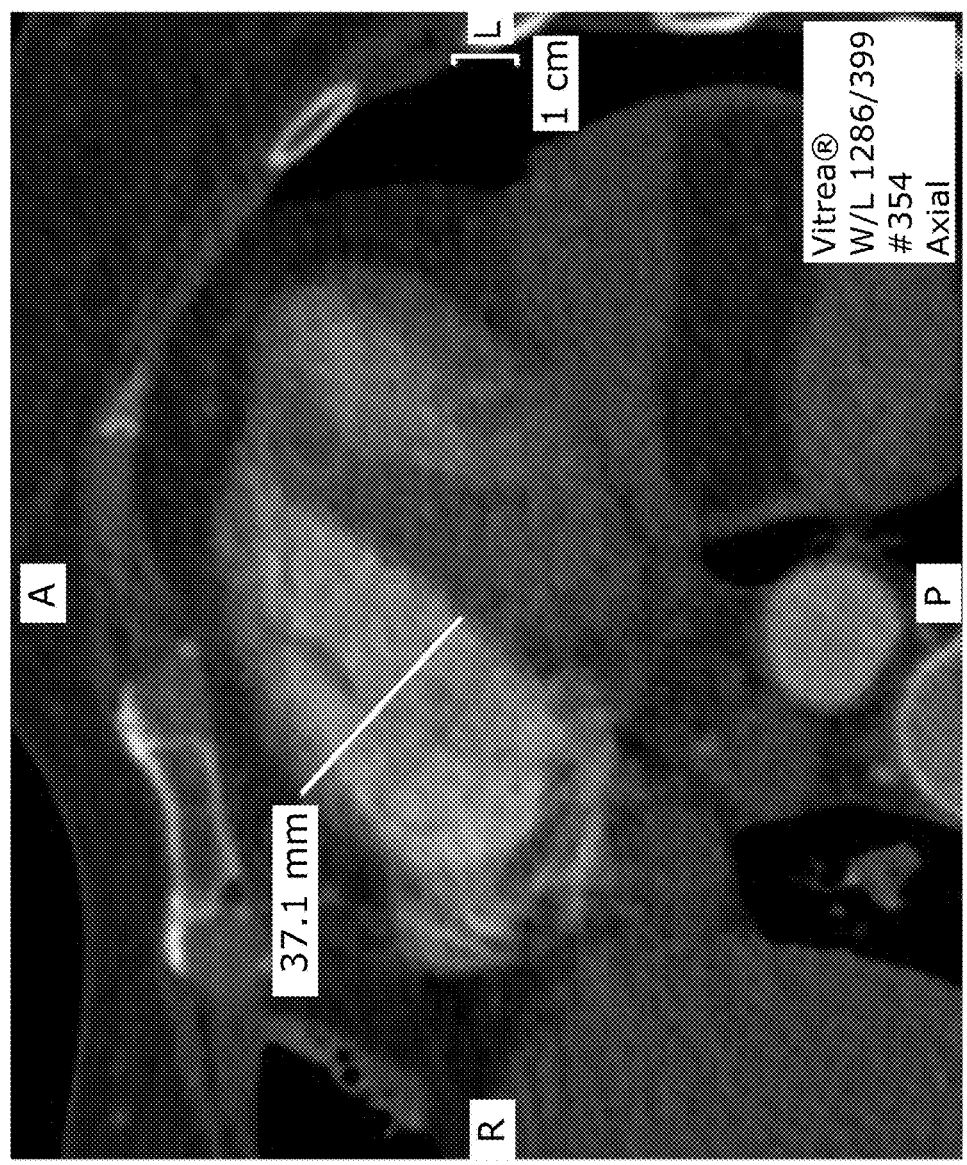
FIG. 2 is a comparison between manual (top row) and automated (bottom row) diameters for the right ventricle (left) and left ventricle (right)

The proposed method underestimates the RV diameter by a mean value of about 4.7 mm (9.8%) and the LV diameter by a mean of about 2.3 mm (5.1%) for LV, p<0.001. This underestimation is mainly due to imaging artifacts and low contrast between trabeculae and other endocardial structures with respect to the myocardium, being those tissues consistently excluded in our segmentation and not excluded by the radiologist. A qualitative example is shown in FIG. 2. On the other hand, the comparison of the manually estimated ratio and the automatically estimated one is not statistically significant (difference 0.02 (1.8%), p=0.08). This is due to the cancellation of both underestimation effects when computing the ratio.

Figure 2B:
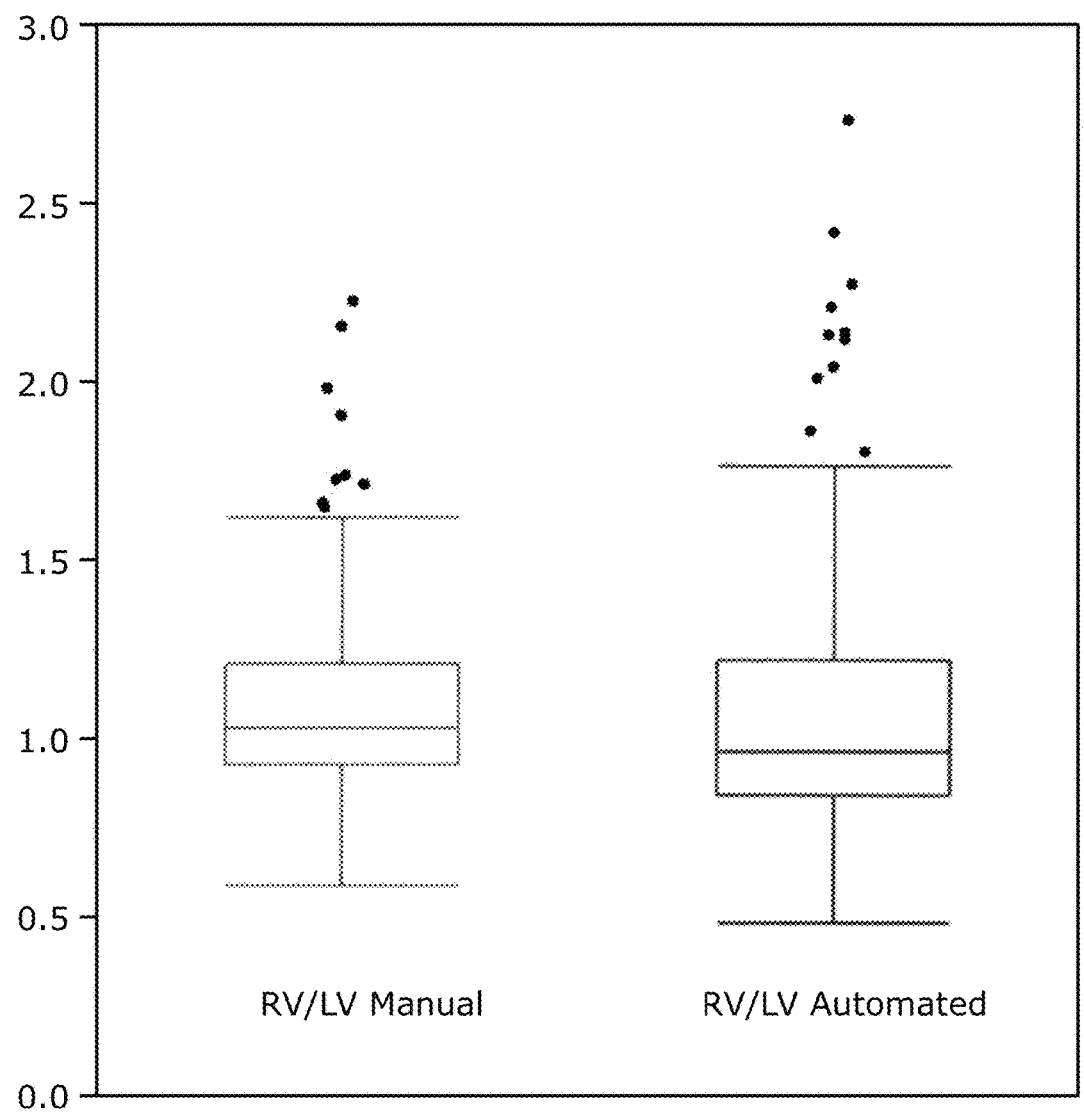
FIG. 2B is a Tukey plot of the manual and automatically computed RV/LV diameter ratios.
Figure 3:
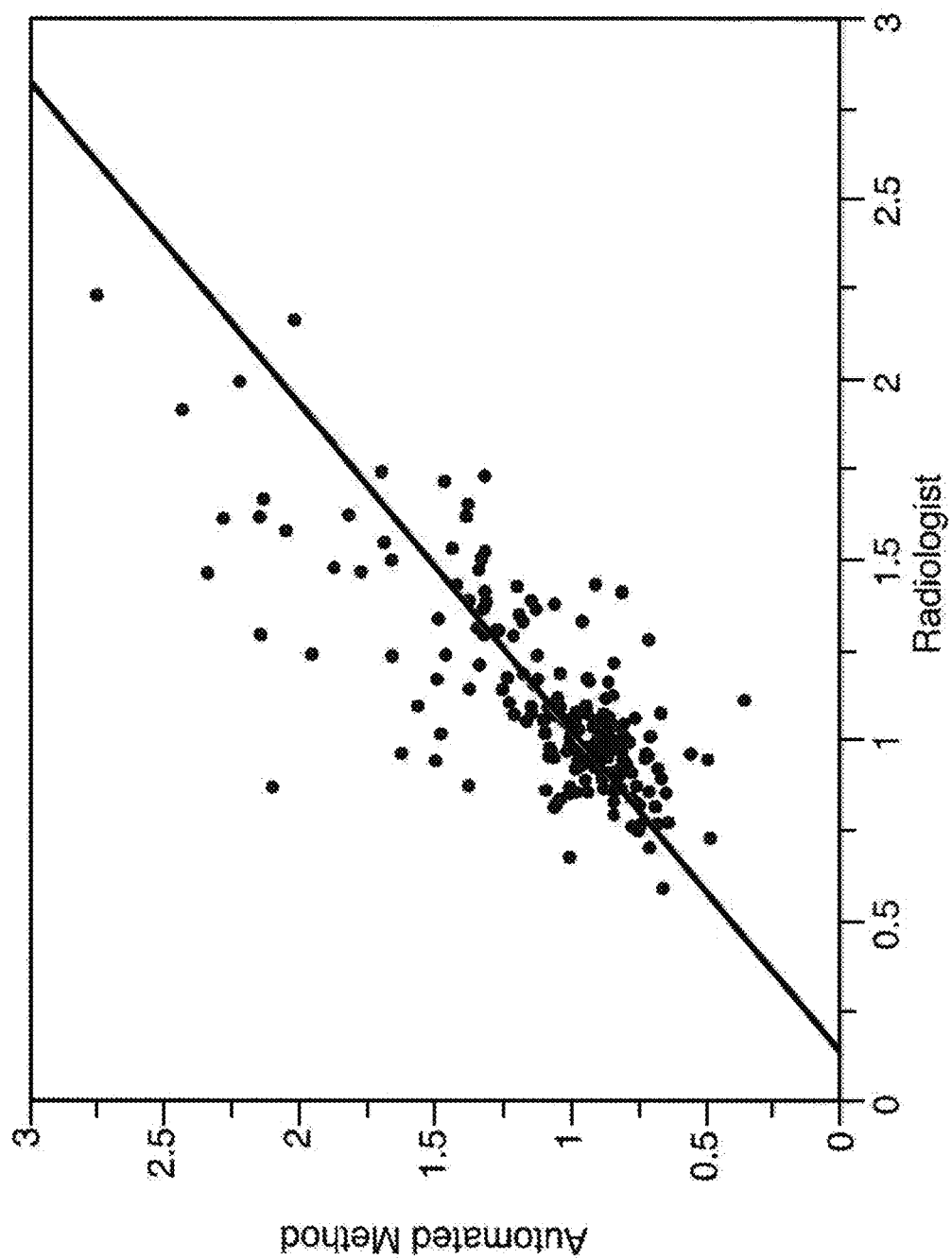
FIG. 3 is a comparison of automated and manually computed RV/LV diameter ratios. A linear model is fitted to the data. The intercept's value is −0.16, the slope is 1.11, Person's correlation coefficient is R=0.81, 95% CI [0.76 0.86], and Spearman's rank correlation coefficient is 0.71. Root mean square error is 0.22.
Figure 3A:
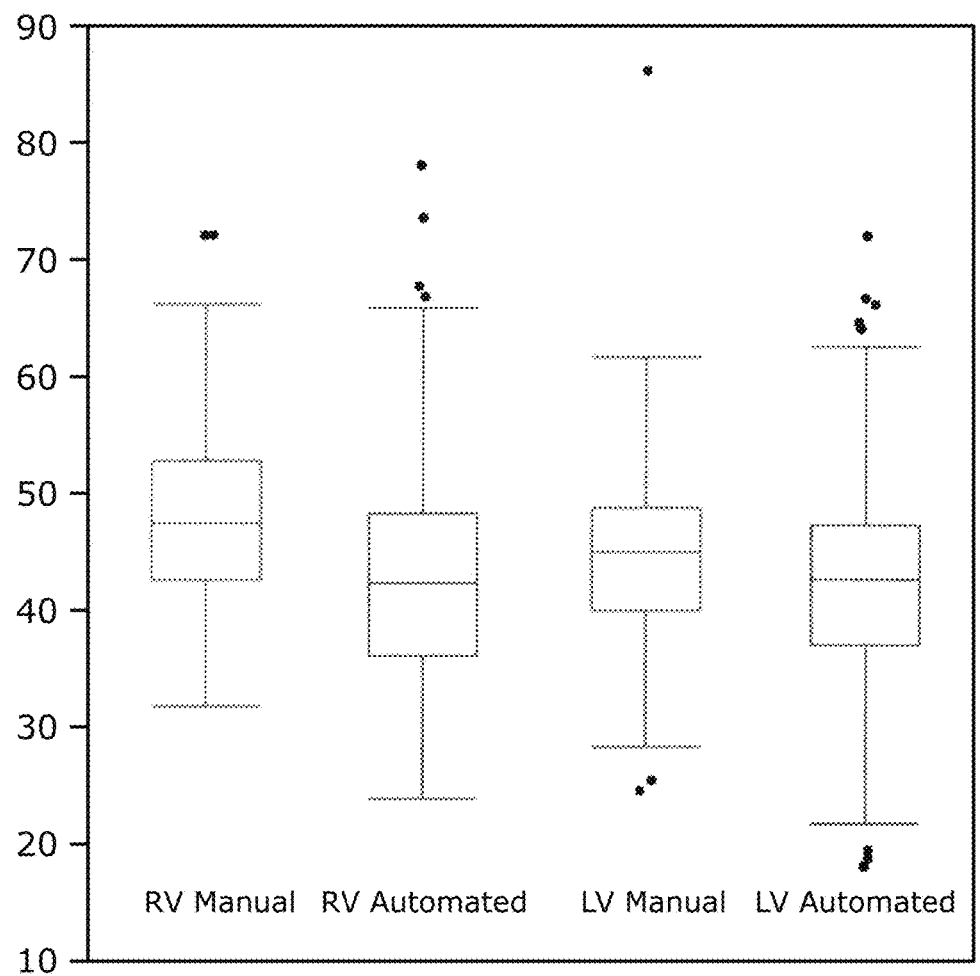
FIG. 3A is a Tukey outlier box plot of manually and automated extracted ventricular diameters. The box is placed at the median of the distribution. Top and bottom limits of the boxes represent 1st and 3rd quartiles of the data respectively. Whiskers length is 1.5 inter-quartile distances. Individual dots are considered outliers. The median of both the automatically computed RV and LV are lower than their manual counterparts.

Inter-reader variability assessed in 30 cases with dual readings had a Pearson correlation coefficient of 0.73, 95% CI [0.50 0.86] and Spearman correlation of 0.75. The linear correlation plot of the automated diameter ratio versus the manual one is shown in FIGS. 2B, 3 and 3A. The linear fit has a small intercept (−0.15) and a slope of 1.11 (p<0.001). Pearson's correlation coefficient between manual and automated diameter ratios is 0.81, 95% CI [0.79 0.86] and Spearman's rank correlation coefficient is 0.71. The correlation coefficients of the automated method with respect to the manual one are comparable to those obtained for the inter-reader variability.

Figure 4:
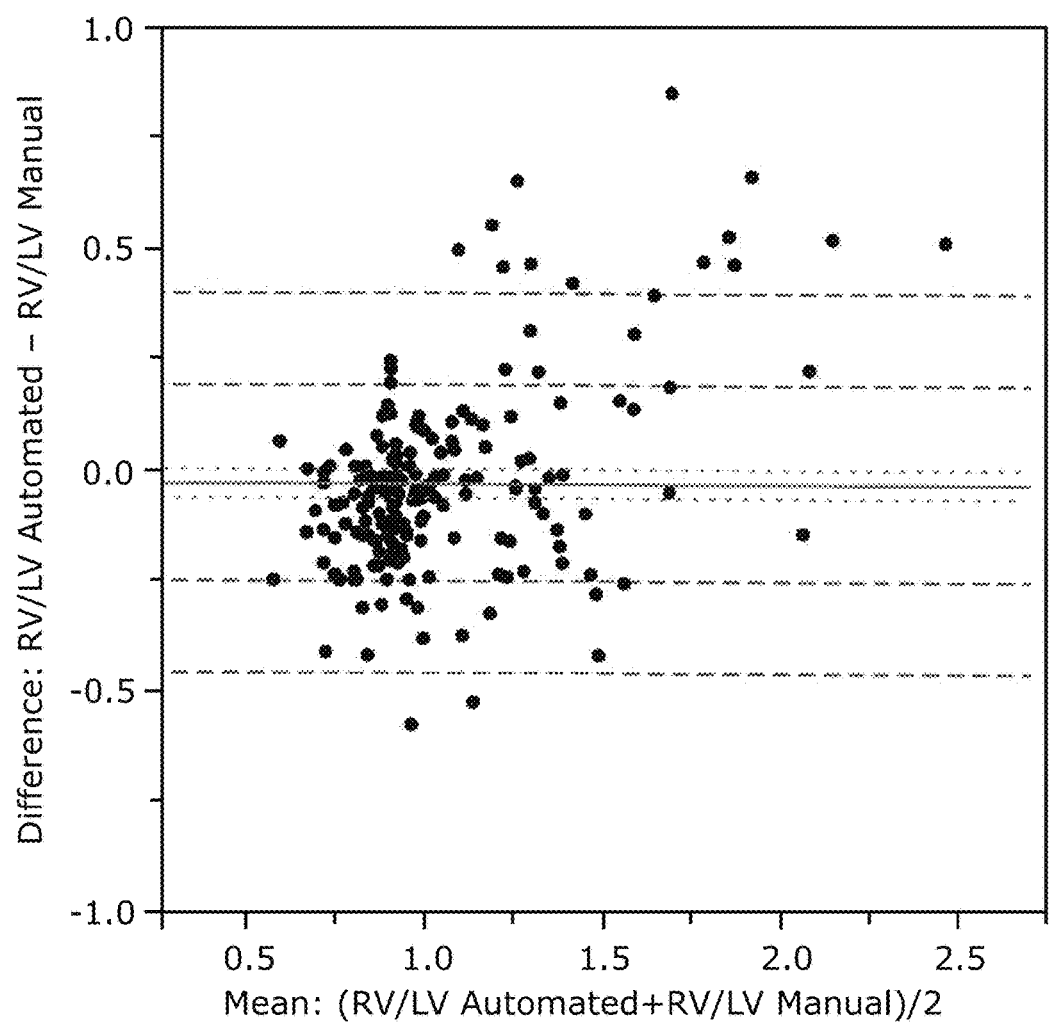
FIG. 4 is a Bland-Altman comparison of the manually estimated RV/LV ratio and the automatically computed one. In this figure the red line: mean difference, dotted red line: mean difference 95% CI, dashed green line: 1.96*STD (radiologists), dashed blue line: 1.96*STD (manual VS automated). The small mean difference −0.023 (95% CI [−0.061 0.003]) with p-value=0.08 shows that the measurements are not significantly different.
Figure 6:
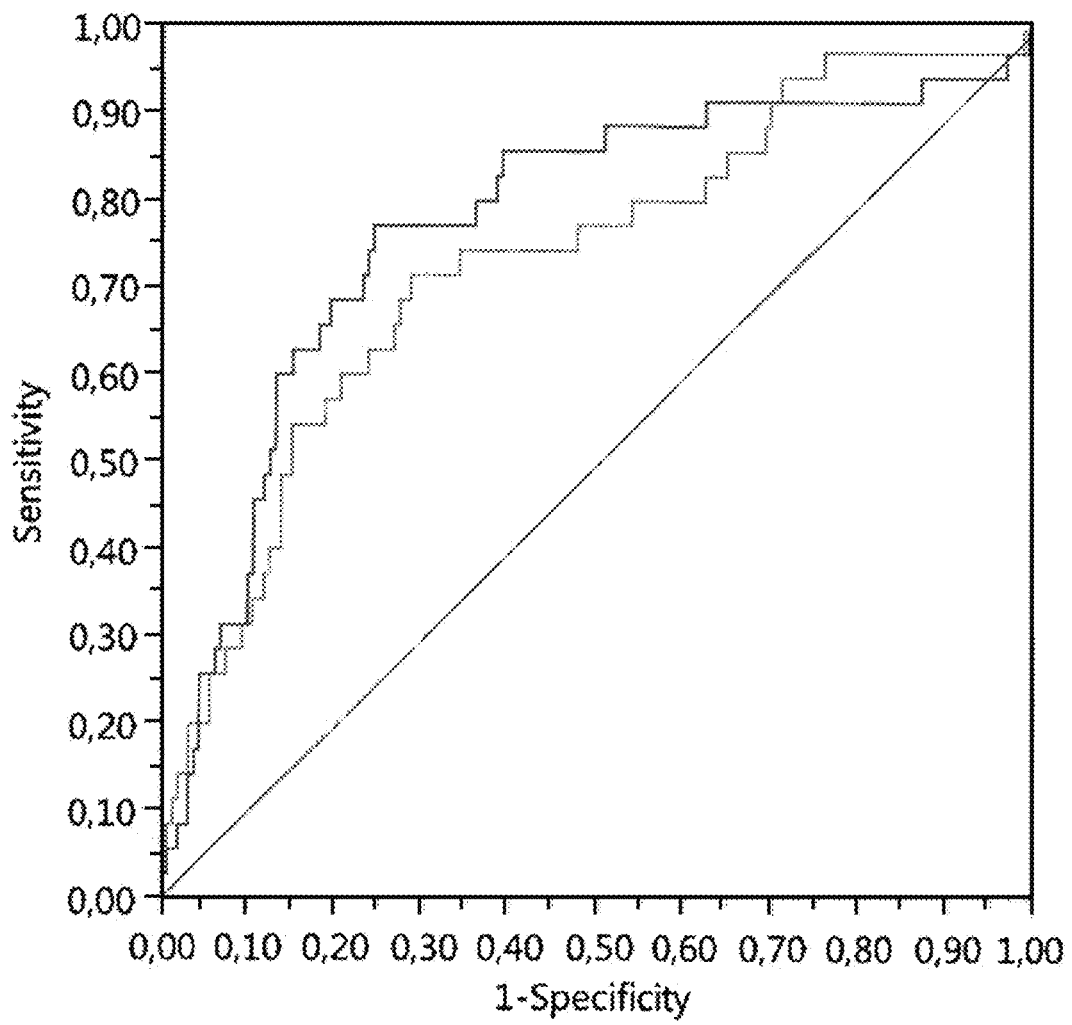
FIG. 6 is an ROC curve for the manual (blue) and automated (red) RV/LV diameter ratios when used to predict 30 days PE-related mortality or the need of intensive therapies. In this figure, the area under the curve is 0.78 for the manual method and 0.75 for the automated one.

Bland-Altman analysis of both methods is shown in FIGS. 4 and 6. Such analysis is performed to show that there is a non-significant bias of one method with respect to another. The mean difference is very small: −0.023 (95% CI [−0.059 0.013]). Blue dashed lines define 95% confidence interval of the difference of the automatically computed RV/LV diameter ratio and the manual one, with values [−0.47 0.46]. Green dashed lines show inter-reader 95% CI as reference. 81.6% (147/183) cases are within the limits of inter-reader variability.

Prognostic Value of the RV/LV Ratio

Table 2 summarizes the mean values of the automated and manual RV/LV diameter ratios extracted for the two different medical outcomes.

TABLE 2

Means of the RV/LV ratios computed manually and automatically for different medical outcomes. P-values are computed with Wilcoxon's rank sums tests.

| | 30 days PE-Related Death | | | 30 days PE-Related Death or Intensive Therapies | | |
|---|---|---|---|---|---|---|
| | + | − | p-value | + | − | p-value |
| Manual | 1.31 | 1.08 | 0.0006 | 1.32 | 1.05 | <0.0001 |
| Automated | 1.32 | 1.05 | 0.0062 | 1.36 | 1.02 | <0.0001 |

Patients that die from PE have a mean RV/LV diameter ratio greater than those that survive or die by other causes, both using manually (1.31 vs. 1.08, p=0.0006) and automatically estimated ratios (1.32 vs. 1.05, p=0.006). Patients that die from PE or require intensive therapies also have a greater average RV/LV diameter ratio, both manual (1.32 vs. 1.05, p<0.0001) and automated (1.36 vs. 1.02, p<0.0001) than those that survive without intensive therapies or die from other condition.

Figure 5:
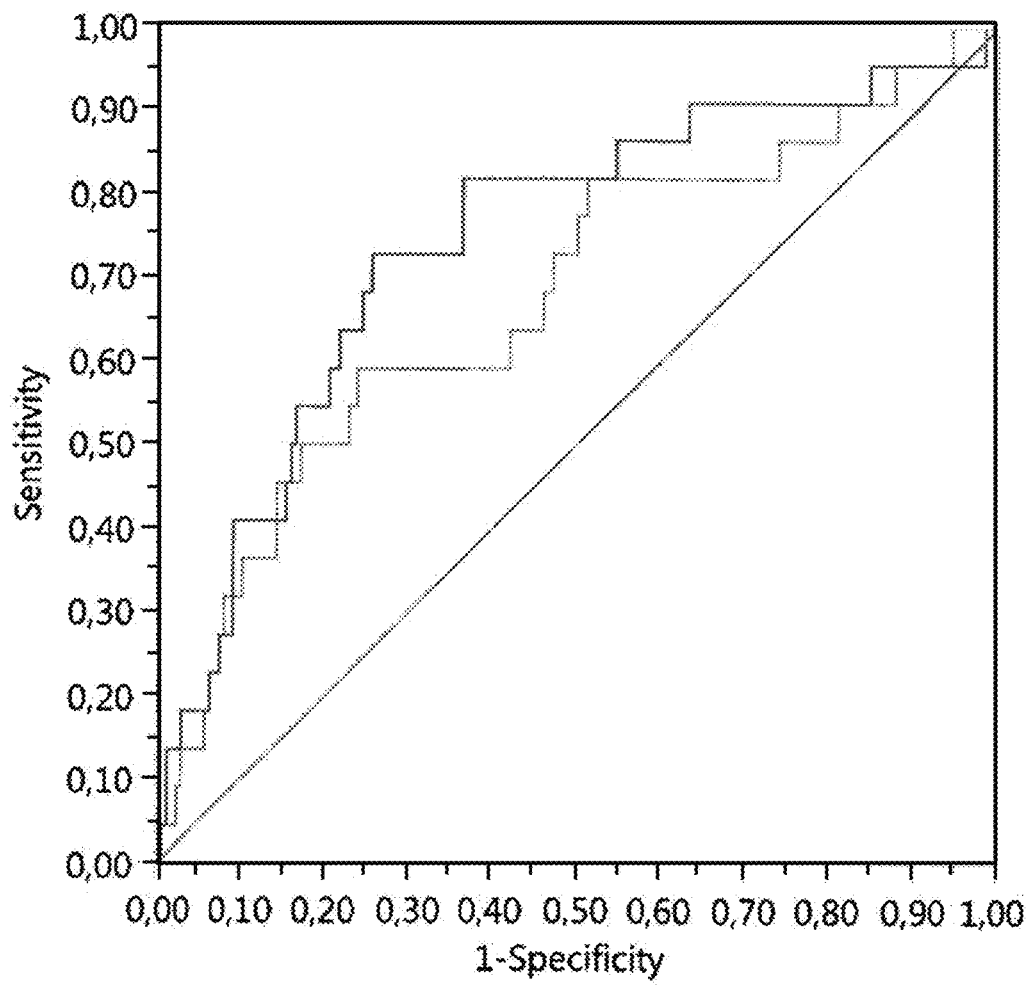
FIG. 5 is a ROC curve for the manual (blue) and automated (red) RV/LV diameter ratios when used to predict 30 days PE-related mortality. In this figure, the area under the curve is 0.75 for the manual method and 0.72 for the automated one.

FIG. 5 shows the ROC curves of manually and automatically estimated RV/LV diameter ratios for 30-days PE-related mortality as medical outcome. Age and sex are not significant predictors of 30-days PE-related mortality, with p-values of 0.09 and 0.35 for the manual ratio and 0.13 and 0.61 for the automated one. However, RV/LV diameter ratio is a significant predictor of 30-days PE-related mortality, with p-value of 0.0005 for the manual method and 0.008 for the automated one. AUC analysis shows that manual and automated RV/LV diameter ratios are very close-by in predictive value with values of 0.75 (95% CI [0.61 0.85]) and 0.72 (95% CI [0.58 0.82]) respectively. The Chi-Square test cannot establish that the models are different (p-value of 0.408).

Similarly, FIG. 6 shows the receiver operating characteristic (ROC) curves of manually and automatically estimated RV/LV diameter ratios for the composite outcome of 30 days PE-related death or the need of intensive therapies. Age and sex are not significant predictors of 30-days PE-related mortality, with p-values of 0.39 and 0.88 for the manual ratio and 0.50 and 0.77 for the automated one. However, RV/LV diameter ratio is a significant predictor of 30-days PE-related mortality, with p-values <0.0001 both methods. AUC analysis shows that manual and automated RV/LV diameter ratios are very close-by in predictive value with values of 0.78 (95% CI [0.67 0.86]) and 0.75 (95% CI [0.64 0.83]) respectively. The Chi-Square test cannot establish that the two predictive models are different (p-value of 0.28).

Areas under the curves and p-values are summarized in Table 3.

TABLE 3

Area under the curve comparison for the different methods and medical outcomes.. P-values obtained with a Chi-Square Goodness of Fit Test.

| | 30 days PE-related death (95% CI) | 30 days PE-Related Death or Intensive Therapies (95% CI) |
|---|---|---|
| Manual | 0.75 [0.61 0.85] | 0.78 [0.67 0.86] |
| Automated | 0.72 [0.58 0.82] | 0.75 [0.64 0.83] |
| Difference | 0.027 [−0.09 0.04] | 0.031 [−0.09 0.03] |
| P > ChiSq | 0.408 | 0.280 |

Although the RV/LV ratio has been shown to be a good prognostic biomarker for patients suffering from acute PE, it is not routinely reported at the radiology units of hospitals. This could be due to the time that it takes to compute such ratio (between 2 and 5 minutes). To prevent such increase in radiologists' time, recent research has focused on subjective evaluation of right ventricular enlargement. However, such evaluation will depend on radiologists' training. An algorithm that reliably and completely automatically computes the RV/LV diameter ratio will provide an objective metric without incurring extra radiologists' time.

Our results show that the automated algorithm for determining the RV/LV axial diameter ratio from CTPA in patients with acute PE has high accuracy when compared to measurements made by radiologists and has non statistically significant difference predictive value with respect to manual axial RV/LV diameter ratio for two different clinical outcomes: (i) 30 days PE-related mortality and (ii) the composite outcome of 30-days PE-related mortality or the need of intensive therapies. This CAD system enables automated objective reporting of the axial RV/LV diameter ratio. In a clinical setting, the radiologist could be presented with images of the diameters and could evaluate very quickly if they are properly placed or not. A prototype is readily implemented as an OSIRIX plugin and its evaluation in terms of usability and performance is being considered as a future work. Each new case RV/LV is computed in background mode taking about 4 minutes for total computation.

The dataset where we have evaluated our algorithm is representative of day-to-day clinical practice. CTPA images were acquired with two different scanners with 16-detectors and 64-detectors respectively. There is no ECG gating in CTPA, therefore there are strong motion artifacts in the images of the hearts. ECG gating is not recommended for the diagnosis of PE due to the increase in radiation exposure. Furthermore, the iodinated contrast agent can enhance the right atrium and ventricle, the left atrium and ventricle or all of the previous chambers, depending on different factors such as the acquisition time with respect to contrast administration, or the heart rate of the patient. Shadow artifacts may also appear close to regions where the contrast agent is very dense. Not only image acquisition and artifacts are challenging, but also the database has a large inter-subject variability, with patients suffering from different clinical conditions, such as malignancies, atelectasis, fibrosis, pleural effusions, cardiomegaly, etc. Furthermore, ventricles can rarely be considered as having homogeneous contrast, since structures such as the travecular-papilary muscle complex can vary the image properties of the ventricle.

Several algorithmic insights are used to accommodate for imaging artifacts and inter-subject and ventricular variability. First, the detection technique according to the various embodiments of the present disclosure is very robust, able to detect hearts at different scales and shapes by using high dimensional image descriptors based on image gradients, a multi-scale detection technique, expected locations of the heart with respect to the images and a strong clustering algorithm. Second, the septum detection is very stable due to the constrained area of the image where it is searched. Third, the level-set segmentation method prevents leakages by imposing local curvature constraints. Last, the diameter estimation algorithm takes into account the shape of the segmentation to find the atrioventricular valve and prevent calipers from being placed in the atrium. All these features are key to make the final measurements robust enough to compensate for image perturbations and inter-subject variability.

Algorithm: Estimation of the RV/LV

Input:
    CTPA study (set of DICOM images)
    Models for heart detection, one for the right ventricle and another for the left ventricle (learned from training data using [1])
    Location priors
    Size priors
Output:
    Real value representing the RV/LV diameter ratio Algorithm:

1. Load the models, the location priors and the CTPA study
2. Detect ventricle locations in the CTPA study by:
    a. For each axial slice of the CTPA study:
        i. Creating a Gaussian pyramid of the slice
        ii. Detecting the Right Ventricle using the right ventricle model. Each detection is a duplet of coordinates (x, y) representing the corners of a box that encompasses the ventricle and a score (s) representing how much the detection resembles the model. The detection algorithm is described in [Felzenszwalb PF, Girshick RB, McAllester D (2010) Cascade object detection with deformable part models. Computer vision and pattern recognition (CVPR), 2010 IEEE conference on. pp. 2241-2248. Available: http://ieeexplore.ieee.org/xpls/abs_all.jsp?arnumber=5539906. Accessed 23 October 2012.].
        iii. Idem for Left Ventricle.
        iv. Storing the detections for further processing
    b. For each ventricle:
        i. Selecting boxes that are coherent with size and location priors by:
            1. For each axial slice selecting the 25 detections with highest score s
            2. Removing detections that are too big or too small to be considered a ventricle according to the size priors
            3. Computing the center of mass of the pixels of the CTPA image whose value is greater than 300 Hounsfield Units (HU) in the plane x, y
            4. Removing detections whose distance to the center of mass is greater than the distance allowed by the location priors.
            5. If there are no boxes remaining, repeat 2.a) and 2.b.i) with a less restrictive model.
        ii. Clustering boxes that are similar
            1. Assign to each detection surviving from 2.b a vector containing the coordinates of its center and the area of the detection: [x, y, a].
            2. Cluster such vectors using the MeanShift algorithm
            3. If there are several detections in the same cluster in the same axial slice, select the detection with higher score s value, as obtained in 2.a.ii
        iii. Associate to each cluster the score of the sums of the scores of the detections in the cluster (s) divided by two plus the number of detections in the cluster.
        iv. Selecting the cluster with highest score as defined in 2.b.iii
        v. Place a 'seed point' in the image for each detection in the cluster selected in 2.b.iv. The seed is positioned relative to the centroid of the detection, depending if the detection is of the right ventricle or the left ventricle.
        vi. Finding the bounding box of the detections of the cluster of 2.b.iv
3. Detecting the inter-ventricular septum by modeling it as a plane. The plane is defined by a direction dv and a point pt. The plane is estimated by:
    a. Computing all lines between right ventricular seeds and left ventricular seed points (Seed points computed in 2.b.v)
    b. Find the minimum value of the voxels of the image along the line. Store the coordinate of such minimum value.

c. Find the volume that contains all the coordinates of 3.b.
d. For a set of predetermined scales se between 5 and 12:
   i. Compute the hessian matrix of the image in the volume defined on 3.c at the given scale se
   ii. Normalize such hessian matrix by the scale.
   iii. Compute the eigen-values (I1,I2,I3) of 3.d.ii
   iv. Compute the absolute value of the eigen-values of 3.e.iii Let's call them Ia1,Ia2,Ia3.
   v. Compute the value vd(sc) = $(1-e^{\{-(Ia1^2+Ia2^2+Ia3^2)\}}) * (Ia3-Ia2)/(Ia3+Ia2)$
   vi. Assign 0 to voxels of vd(sc) that correspond to values of I3 < 0
   vii. Save the eigen-vectors associated to vd(sc): evd(sc)
e. Find the maximum across scales of vd(sc): vdmax = max_{sc}(vd(sc))
f. Find the 2% maximal points of vdmax and their associated eigenvectors: evdmax: ptmax, vmax
g. Obtain the median vmedian direction of the set of vectors vmax. Such median is the direction of the estimated septum: dv. Obtain the vector, vp, that is closest in direction to vmedian . The point associated to such vector is the point that defines the septum: pt 4. For each ventricle:
   a. Find the segmentation of the ventricle with the level-set algorithm described in [Jimenez-Carretero D, Fernandez-de-Manuel L, Pascau J, Tellado JM, Ramon E, et al. (2011) Optimal multiresolution 3D level-set method for liver segmentation incorporating local curvature constraints. Engineering in Medicine and Biology Society, EMBC, 2011 Annual International Conference of the IEEE. pp. 3419-3422. Available: http://ieeexplore.ieee.org/xpls/abs_all.jsp?arnumber=6090925. Accessed 23 October 2012.], using as initialization the seeds obtained in 2.b.v and using the septum computed in 3.g as a constraint.

5. Place the caliper in the segmentation of the right ventricle, perpendicular to the septum. Such is done by:
   a. For each axial slice of the segmentation, obtain the maximum caliper by:
      i. Measuring the segmentation perpendicularly to the septum at all positions along the septum at intervals dx
      ii. Analyze such measurements by:
         1. Fitting a $10^{th}$ order polynomial (p) to the measurements
         2. Computing the derivative of the polynomial (pd) and its roots (rpd). Retain only real roots.
         3. Computing the second derivatives of the polynomial (pdd) and their roots (rpdd). Retain only real roots.
         4. Removing roots from rp and rpd that are very close to the extremes (very close defined as being less than 5*dx to the ends of the segmentations).
         5. Selecting the right root of the polynomial according to the following decision tree:
            a. If there are three or more roots in rpd and pdd on the first root is lower than 0 and pdd on the second root is greater than 0 and the pdd at the third root is lower than 0, take as position of the caliper the first root of rpd.
            b. Else, if there are at least two roots in rpd and and the pdd on the first root is lower than 0 and the pdd on the second root is greater than 0, take as position of the caliper the position of the first root of rpd
            c. Else, If there is at least one root in rpdd, the value of pd at that root is greater than 0 and small, take as position of the caliper the value that root
            d. Else, If there is at least one root in rpd and pdd in that root is lower than 0, take as position of the caliper the position of the first root of rpd
            e. Else, produce an error message.
         6. Return as value of the caliper, the caliper at the root selected in 5.ii.5
   b. The final caliper is the maximum value of the calipers computed at each axial slice in 5.a.

6. Place the left caliper in the segmentation of the left ventricle perpendicular to the septum. Such is done by:
   a. For each axial slice of the segmentation, obtain the maximum caliper by:
      i. Measuring the segmentation perpendicularly to the septum at all positions along the septum at intervals dx
      ii. Analyze such measurements by:
         1. Fitting a $10^{th}$ order polynomial (p) to the measurements
         2. Computing the derivative of the polynomial (pd) and its roots (rpd). Retain only real roots.
         3. Computing the second derivatives of the polynomial (pdd) and their roots (rpdd). Retain only real roots.
         4. Removing roots from rp and rpd that are very close to the extremes (very close defined as being less than 5*dx to the ends of the segmentations).

-continued

> 5. If the value of pdd at the first root of rpd is lower that 0, return the value of the caliper at that root, else, produce an error message.
> 
> b. The final caliper is the maximum value of the calipers computed at each axial slice.
> 
> 7. Finally, return the length of the caliper estimated for the right ventricle divided by the length of the caliper estimated for the left ventricle.

Although the various teachings of the present disclosure are focused on the axial computation of the RV/LV diameter ratio, other manners of computing such ratio have been proposed in the literature, such as volumetric measurements or 4-chamber reformatted images. However, axial computation of the RV/LV ratio has been disclosed herein because of its simplicity to review and because it does not require post-processing or a dedicated workstation to validate or correct the ratios that have been found. However, since volumetric representations of the ventricles are obtained, volumetric RV/LV relationships can be evaluated or images can be automatically reformatted to compute 4-ch RV/LV ratio.

In summary, the various embodiments of the present disclosure provide an algorithm that is able to read a CTPA scan and output an automated measurement of the RV/LV diameter ratio with high accuracy and with the same prognostic value as the ratio a radiologist would find. Having a tool that reliably and transparently computes such ratio and includes it into the medical report can help better patient stratification, with the ultimate aim of identifying those patients who might benefit from more aggressive fibrinolytic therapies as well as other intensive therapies.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the present disclosure as set forth in the appended claims and their legal equivalents.

In a preferred illustrative embodiment identified as "embodiment 1", there is presented a method for determining the prognosis of a patient suffering from pulmonary embolism, the method comprising:

receiving images of the patient containing at least the heart and the lungs;

inferring ventricles of a heart of the patient;

estimating an inter-ventricular septum;

measuring the ventricles of the heart in lines perpendicular to the interventricular septum; and reporting the value of the division of a maximum measurement for a right ventricle to a maximum measurement for a left ventricle.

Embodiment 2

The method of embodiment 1 wherein reporting comprises displaying images of the right ventricle with the maximum measurement overlaid and of the left ventricle with the maximum measurement overlaid.

Embodiment 3

The method of embodiment 2 further comprising an interface where the results are displayed that is configured to receive input to modify at least one of the maximum measurement for the right ventricle and the maximum measurement for the left ventricle.

Embodiment 4

The method of embodiment 3 further comprising reporting automatically the value of the division of the maximum measurement for the right ventricle and the maximum measurement for the left ventricle to the electronic medical record of the hospital.

Embodiment 5

A method for determining the prognosis of a patient suffering from pulmonary embolism, the method comprising:

receiving patient data containing at least images of the heart; and reporting a risk index for the patient a given clinical outcome based on the images of the heart.

Embodiment 6

The method of embodiment 5, further comprising:

based on the images of the heart, inferring ventricles of the heart;

estimating the inter-ventricular septum;

measuring the ventricles of the heart in lines perpendicular to the interventricular septum.

Embodiment 7

The method of embodiment 6, wherein patient data further comprises data regarding a clinical state of the patient for retrieving another derived measure of prognosis.

Embodiment 8

A system for determining the prognosis of a patient suffering from pulmonary embolism, comprising:

a tangible storage medium readable by a processing circuit and storing instructions for execution by the processing circuit, the instructions configured to:

receive patient data that includes a pulmonary embolism status;

create a model of a heart of the patient based on the patient data with at least information regarding two ventricles;
determine a ratio of sizes of the ventricles; and
output the ratio.

The invention claimed is:

1. A method for computing the Right Ventricle:Left Ventricle diameter ratio in a patient, the method comprising:
receiving a plurality of axial images of the patient showing at least the heart, forming a three-dimensional image formed by voxels;
automatically estimating, via a computer system, in the three-dimensional image the location and shape of the contour of the ventricles of the heart of the patient, said estimation comprising;
providing an axial slice formed as a 2-dimensional model of the shape of the right ventricle and an axial slice as a 2-dimensional model of the shape of the left ventricle by training a machine learning based algorithm;
detecting in each axial slice the shape and location of the right ventricle and the shape and location of the left ventricle by said trained algorithm;
for each detected ventricle in each axial slice, providing a 2-dimensional bounding box and a score representing the fitness of the detection to each model;
selecting detected ventricles that are coherent with size and locations of 2-dimensional models previously recorded when modeling;
clustering detected ventricles according to the similarities on position of the detections, their sizes and their aspect ratio;
ranking clusters and selecting the cluster with the highest score for the left and the right ventricle; and
for the left and for the right ventricles of the selected cluster, locating a seed point in the axial image related to the centroid of said selected ventricle;
automatically estimating, via the computer system, in the three-dimensional image the location of the inter-ventricular septum of the heart of the patient modeled as a plane from the seed points;
automatically estimating, via the computer system, the diameter of the ventricles of the heart as the maximum width of the contour of each ventricle measured in lines perpendicular to the interventricular septum; and
reporting the value of the division of the maximum measurement for a right ventricle to a maximum measurement for a left ventricle.

2. The method according to claim 1, wherein detected ventricles are coherent with size and locations of models when:
absolute value of the difference between the area of the detected ventricle and the model is less than a predetermined predefined value; and
absolute value of the difference between the position of the mass centre of the image and the centroid of the detected ventricle is less than a predefined value.

3. The method according to claim 1, wherein automatically estimating the location of the inter-ventricular septum of the heart modeled as a plane comprises:
for each pair of seeds, the seed of the right ventricle and the seed of the left ventricle, computing the line connecting the pair of seeds;
for each line, calculating the location of the voxel wherein a three-dimensional image intensity is a maximum if an intensity of the voxels representing the septum is higher than an intensity of the voxels representing the ventricle, or a minimum if the intensity of the voxels representing the septum is lower than the intensity of the voxels representing the ventricle;
defining a volume comprised by the voxels previously calculated;
computing the plane that represent the inter-ventricular septum form from the plurality of voxels of such volume, wherein said computing comprises:
for each voxel, computing the hessian matrix of the three-dimensional image at such voxel location being the hessian matrix $$\begin{pmatrix} H_{xx} & H_{xy} & H_{xz} \\ H_{yx} & H_{yy} & H_{yz} \\ H_{zx} & H_{zy} & H_{zz} \end{pmatrix}$$

wherein $H_{ij}$, i,j=x,y,z represents the convolution of the image with the second derivative along the dimensions i,j of a gaussian kernel of a predetermined sigma;
for each voxel, computing the eigenvalues and eigenvectors of the associated hessian matrix;
for each voxel determining a score proportional to a plate-like structure traversing said voxel;
selecting a predetermined number of voxels within the volume with the highest score;
calculating the median direction of the eigenvectors of the selected voxels, said median direction being the direction of the estimated septum; and
defining the plane of the septum as the plane containing the voxel whose eigenvector is closest in direction to the median direction and the normal of the plane being the median direction.

4. The method according to claim 1, wherein each ventricle is automatically segmented, via the computer system, by evolving a contour form from at least one seed point by means of a level-set algorithm under constraints over the three-dimensional image.

5. The method according to claim 4, wherein the three-dimensional image constraints are defined by a learning pre-process wherein the level-set algorithm is run over a plurality of cases taken from an evaluation dataset.

6. The method according to claim 1, wherein automatically estimating, via the computer system, the diameter of the ventricles further comprises:
for each axial image, determining the septum line as the intersection between the plane of the septum and the axial image;
defining the cross measurement of the ventricle as the distance value between the closest point of the contour and the farthest point of the contour along a line perpendicular to the septum line at certain points $x_i$ along the septum line from the apex to the atrium;
defining a discrete function $p_i=f(x_i)$, i=1 . . . n for a predetermined number of sample points n, wherein $x_i$ have cross measurements $p_i$;
fitting the discrete function $p_i=f(x_i)=1 . . . n$ by a polynomial of order n; and
determining the estimated diameter or caliper as the value of the polynomial at the at least one root of the first derivative of the polynomial.

7. The method according to claim 6, wherein the estimation of the right ventricle diameter further comprises:

defining a closed domain of the polynomial as the domain where the cross measurement exists;

calculating the first derivative $p_{n-1}'(x)$ from $p_n(x)$ and the roots of the first derivative (rpd);

calculating the second derivative $p_{n-2}''(x)$ from $p_n(x)$ and the second derivative's roots (rpdd);

selecting the root of the polynomial for the estimation of the diameter of the right ventricle according to the following criteria:

in the event that there are three or more roots in $p_{n-1}'(x)$, and $p_{n-2}''(x)$ on the first root, being the roots sorted from the left boundary to the right boundary of the closed domain, is lower than 0, and $p_{n-2}''(x)$ on the second root is greater than 0, and the $p_{n-2}''(x)$ at the third root is lower than 0, taking as root of the polynomial for the estimation of the diameter of the right ventricle the first root of $p_{n-1}'(x)$;

in the event that there are at least two roots in $p_{n-1}'(x)$, and the $p_{n-2}''(x)$ on the first root is lower than 0, and the $p_{n-2}''(x)$ on the second root is greater than 0, taking as root of the polynomial for the estimation of the diameter of the right ventricle the position of the first root of $p_{n-1}'(x)$;

in the event that there is at least one root in $p_{n-2}''(x)$, the value of $p_{n-1}'(x)$ at the first of these roots is greater than 0 and smaller than a predetermined threshold, taking as root of the polynomial for the estimation of the diameter of the right ventricle the value of that root; and in the event that there is at least one root in $p_{n-1}'(x)$ and $p_{n-2}''(x)$ in the first of the roots is lower than 0, taking as root of the polynomial for the estimation of the diameter of the right ventricle the position of the first root of $p_{n-1}'(x)$.

8. The method according to claim 7, wherein after calculating the roots of the first derivative $p_{n-1}'(x)$ and the roots of the second derivative $p_{n-2}''(x)$, those roots closer than a predetermined value to the extremes of the domain are removed.

9. The method according to claim 6, wherein the estimation of the left ventricle diameter further comprises:

defining a closed domain of the polynomial as the domain where the cross measurement exists;

calculating the first derivative $p_{n-1}'(x)$ from $p_n(x)$ and the roots of the first derivative (rpd);

calculating the second derivative $p_{n-2}''(x)$ from $p_n(x)$ and the roots of the second derivative (rpdd);

determining whether the value of $p_{n-2}''(x)$ at the first root of $p_{n-1}'(x)$ is less than 0; and upon determining that the value of $p_{n-2}''(x)$ at the first root of $p_{n-1}'(x)$ is less than 0, taking said first root of $p_{n-1}'(x)$ as root of the polynomial for the estimation of the diameter of the left ventricle.

10. The method according to claim 9, wherein after calculating the roots of the first derivative $p_{n-1}'(x)$ and the roots of the second derivative $p_{n-2}''(x)$, those roots closer than a predetermined value to the extremes of the domain are removed.

11. The method according to any of claim 6, wherein the maximum distance value between the closest point of the contour and the farthest point of the contour along a line perpendicular to the septum is estimated as the maximum value of the maximum of the polynomials computed at each axial image.

12. A non-transitory computer-readable medium storing code, which when executed by a processor, causes the processor to:

to receive a plurality of axial images of a patient showing at least the heart, forming a three-dimensional image formed by voxels;

to automatically estimating in the three-dimensional image, the location and shape of the contour of the ventricles of the heart of the patient, said estimation comprising;

providing an axial slice formed as a 2-dimensional model of the shape of the right ventricle and an axial slice as a 2-dimensional model of the shape of the left ventricle by training a machine learning based algorithm;

detecting in each axial slice the shape and location of the right ventricle and the shape and location of the left ventricle by said trained algorithm;

for each detected ventricle in each axial slice, providing a 2-dimensional bounding box and a score representing the fitness of the detection to each model;

selecting detected ventricles that are coherent with size and locations of 2-dimensional models previously recorded when modeling;

clustering detected ventricles according to the similarities on position of the detections, their sizes and their aspect ratio;

ranking clusters and selecting the cluster with the highest score for the left and the right ventricle; and for the left and for the right ventricles of the selected cluster, locating a seed point in the axial image related to the centroid of said selected ventricle;

to automatically estimating in the three-dimensional image, the location of the inter-ventricular septum of the heart of the patient modeled as a plane;

to automatically estimating the diameter of the ventricles of the heart as the maximum width of the contour of each ventricle measured in lines perpendicular to the interventricular septum; and to report the value of the division of the maximum measurement for a right ventricle to a maximum measurement for a left ventricle.

13. The non-transitory computer-readable medium of claim 12, wherein the code, when executed by the processor, further causes the processor to:

for each pair of seeds, the seed of the right ventricle and the seed of the left ventricle, to compute the line connecting the pair of seeds;

for each line, to calculate the location of the voxel wherein a three-dimensional image intensity is a maximum if an intensity of the voxels representing the septum is higher than an intensity of the voxels representing the ventricle, or a minimum if the intensity of the voxels representing the septum is lower than the intensity of the voxels representing the ventricle;

to define a volume comprised by the voxels previously calculated;

to compute the plane that represent the inter-ventricular septum form from the plurality of voxels of such volume, wherein said computing comprises:

for each voxel, computing the hessian matrix of the three-dimensional image at such voxel location being the hessian matrix $$\begin{pmatrix} H_{xx} & H_{xy} & H_{xz} \\ H_{yx} & H_{yy} & H_{yz} \\ H_{zx} & H_{zy} & H_{zz} \end{pmatrix}$$

wherein $H_{ij}$, i,j=x,y,z represents the convolution of the image with the second derivative along the dimensions i,j of a gaussian kernel of a predetermined sigma;

for each voxel, computing the eigenvalues and eigenvectors of the associated hessian matrix;

for each voxel determining a score proportional to a plate-like structure traversing said voxel;

selecting a predetermined number of voxels within the volume with the highest score;

calculating the median direction of the eigenvectors of the selected voxels, said median direction being the direction of the estimated septum; and defining the plane of the septum as the plane containing the voxel whose eigenvector is closest in direction to the median direction and the normal of the plane being the median direction.

14. The non-transitory computer-readable medium of claim 12, wherein the code, when executed by the processor, further causes the processor to:

for each axial image, to determine the septum line as the intersection between the plane of the septum and the axial image;

to define the cross measurement of the ventricle as the distance value between the closest point of the contour and the farthest point of the contour along a line perpendicular to the septum line at certain points $x_i$ along the septum line from the apex to the atrium;

to define a discrete function $p_i = f(x_i)$, i=1 ... n for a predetermined number of sample points n wherein $x_i$ have cross measurements, $p_i$;

to fit the discrete function $p_i = f(x_i)$, i=1 ... n by a polynomial of order n; and to determine the estimated diameter or caliper as the value of the polynomial at the at least one root of the first derivative of the polynomial.

15. An electronic device for data analysis, the device comprising a processor; and a computer-readable medium storing computer-executable instructions which, when executed by the processor, causes the processor to:

to receive a plurality of axial images of a patient showing at least the heart, forming a three-dimensional image formed by voxels;

to automatically estimating in the three-dimensional image, the location and shape of the contour of the ventricles of the heart of the patient;

to automatically estimating in the three-dimensional image, the location of the inter-ventricular septum of the heart of the patient modeled as a plane, said estimation comprising;

providing an axial slice formed as a 2-dimensional model of the shape of the right ventricle and an axial slice as a 2-dimensional model of the shape of the left ventricle by training a machine learning based algorithm;

detecting in each axial slice the shape and location of the right ventricle and the shape and location of the left ventricle by said trained algorithm;

for each detected ventricle in each axial slice, providing a 2-dimensional bounding box and a score representing the fitness of the detection to each model;

selecting detected ventricles that are coherent with size and locations of 2-dimensional models previously recorded when modeling;

clustering detected ventricles according to the similarities on position of the detections, their sizes and their aspect ratio;

ranking clusters and selecting the cluster with the highest score for the left and the right ventricle; and for the left and for the right ventricles of the selected cluster, locating a seed point in the axial image related to the centroid of said selected ventricle;

to automatically estimating the diameter of the ventricles of the heart as the maximum width of the contour of each ventricle measured in lines perpendicular to the interventricular septum; and to report the value of the division of the maximum measurement for a right ventricle to a maximum measurement for a left ventricle.

16. The electronic device of claim 15, wherein the computer-executable instructions, when executed by the processor further causes the processor to:

for each pair of seeds, the seed of the right ventricle and the seed of the left ventricle, to compute the line connecting the pair of seeds;

for each line, to calculate the location of the voxel wherein a three-dimensional image intensity is a maximum if an intensity of the voxels representing the septum is higher than an intensity of the voxels representing the ventricle, or a minimum if the intensity of the voxels representing the septum is lower than the intensity of the voxels representing the ventricle;

to define a volume comprised by the voxels previously calculated;

to compute the plane that represent the inter-ventricular septum form from the plurality of voxels of such volume, wherein said computing comprises:

for each voxel, computing the hessian matrix of the three-dimensional image at such voxel location being the hessian matrix $$\begin{pmatrix} H_{xx} & H_{xy} & H_{xz} \\ H_{yx} & H_{yy} & H_{yz} \\ H_{zx} & H_{zy} & H_{zz} \end{pmatrix}$$

wherein $H_{ij}$, i,j=x,y,z represents the convolution of the image with the second derivative along the dimensions i,j of a gaussian kernel of a predetermined sigma;

for each voxel, computing the eigenvalues and eigenvectors of the associated hessian matrix;

for each voxel determining a score proportional to a plate-like structure traversing said voxel;

selecting a predetermined number of voxels within the volume with the highest score;

calculating the median direction of the eigenvectors of the selected voxels, said median direction being the direction of the estimated septum; and defining the plane of the septum as the plane containing the voxel whose eigenvector is closest in direction to the median direction and the normal of the plane being the median direction.

* * * * *